(12) United States Patent
Hancock et al.

(10) Patent No.: US 11,490,950 B2
(45) Date of Patent: Nov. 8, 2022

(54) ISOLATION DEVICE FOR ELECTROSURGICAL APPARATUS

(71) Applicant: CREO MEDICAL LIMITED, Monmouthsire (GB)

(72) Inventors: Christopher Paul Hancock, Bath (GB); Malcolm White, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 326 days.

(21) Appl. No.: 16/633,113

(22) PCT Filed: Aug. 15, 2018

(86) PCT No.: PCT/EP2018/072153
§ 371 (c)(1),
(2) Date: Jan. 22, 2020

(87) PCT Pub. No.: WO2019/034708
PCT Pub. Date: Feb. 21, 2019

(65) Prior Publication Data
US 2020/0352622 A1    Nov. 12, 2020

(30) Foreign Application Priority Data
Aug. 17, 2017   (GB) ..................................... 1713174

(51) Int. Cl.
*H01P 1/213*    (2006.01)
*A61B 18/12*    (2006.01)
(Continued)

(52) U.S. Cl.
CPC ...... *A61B 18/1206* (2013.01); *A61B 18/1815* (2013.01); *A61B 2018/00327* (2013.01);
(Continued)

(58) Field of Classification Search
CPC ...... H01P 1/213; H01P 1/2138; H01P 1/2133; H01P 1/36; H01R 13/646;
(Continued)

(56) References Cited

FOREIGN PATENT DOCUMENTS

| EP | 1658817 A1 * | 5/2006 | ........... A61B 18/042 |
|---|---|---|---|
| GB | 2506377 A | 4/2014 | |
| WO | WO 2015/087051 A1 | 6/2015 | |

OTHER PUBLICATIONS

International Search Report and Written Opinion, Issued by the International Searching Authority corresponding to International Patent Application No. PCT/EP2018/072153, dated Oct. 30, 2018.
(Continued)

*Primary Examiner* — Stephen E. Jones
(74) *Attorney, Agent, or Firm* — ArentFox Schiff LLP (57) ABSTRACT

A combined isolator-diplexer device for supplying radiofrequency (RF) energy and microwave energy obtained from separate sources to a probe via a common signal pathway. The invention combines into a single unit all the necessary components to isolate a microwave channel from an RF channel whilst providing a high withstanding voltage (e.g. greater than 10 kV). The device comprises a waveguide isolator for isolating the microwave channel having a pair of DC isolation barriers arranged therein to provide a pair of series-connected capacitive structures between a ground conductor at an output of the combining circuit and a conductive input section of the waveguide isolator.

14 Claims, 6 Drawing Sheets

(51) Int. Cl.
*A61B 18/18* (2006.01)
*A61B 18/00* (2006.01)
*A61B 18/14* (2006.01)
*H01P 1/36* (2006.01)
*H01R 13/646* (2011.01)

(52) U.S. Cl.
CPC .............. *A61B 2018/00529* (2013.01); *A61B 2018/00577* (2013.01); *A61B 2018/00589* (2013.01); *A61B 2018/00601* (2013.01); *A61B 2018/00785* (2013.01); *A61B 2018/00994* (2013.01); *A61B 2018/1273* (2013.01); *A61B 2018/1412* (2013.01); *A61B 2018/1823* (2013.01); *A61B 2018/1876* (2013.01); *A61B 2018/1892* (2013.01); *H01P 1/2138* (2013.01); *H01P 1/36* (2013.01); *H01R 13/646* (2013.01)

(58) Field of Classification Search
CPC ........... A61B 2018/00577; A61B 2018/00589; A61B 2018/00601; A61B 2018/00785; A61B 2018/00994; A61B 2018/1273; A61B 2018/1412; A61B 2018/1823; A61B 2018/1876; A61B 2018/1892
See application file for complete search history.

(56) References Cited

OTHER PUBLICATIONS

Search Report under Section 17(5), issued in corresponding British Patent Application GB1713174.9, dated Feb. 14, 2018.

\* cited by examiner

ISOLATION DEVICE FOR ELECTROSURGICAL APPARATUS

CROSS-REFERENCE TO RELATED APPLICATIONS

This application is a National Stage entry of International Application No. PCT/EP2018/072153, filed on Aug. 15, 2018, which claims priority to British Patent Application No. 1713174.9, filed on Aug. 17, 2017. The disclosures of the priority applications are hereby incorporated in their entirety by reference.

FIELD OF THE INVENTION

The invention relates to electrosurgical apparatus in which radiofrequency energy is used to treat biological tissue. In particular, the invention relates to surgical apparatus capable of generating radiofrequency (RF) energy for cutting tissue, It may be used in as part of a surgical apparatus which also delivers microwave frequency energy for haemostasis (i.e. sealing broken blood vessels by promoting blood coagulation).

BACKGROUND TO THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, it is also undesirable for a bleed to occur and not to be dealt with as soon as quickly as possible, or in an expedient manner, since the blood flow may obscure the operator's vision, which may lead to the procedure needing to be terminated and another method used instead, e.g. open surgery.

Electrosurgical generators are pervasive throughout hospital operating theatres, for use in open and laparoscopic procedures, and are also increasingly present in endoscopy suites. In endoscopic procedures the electrosurgical accessory is typically inserted through a lumen inside an endoscope. Considered against the equivalent access channel for laparoscopic surgery, such a lumen is comparatively narrow in bore and greater in length. In the case of a bariatric patient the surgical accessory may have a length of 300 mm from handle to RF tip, whereas the equivalent distance in a laparoscopic case can be in excess of 2500 mm.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. When an RF voltage is applied to the tissue matrix, enough heat is generated within the cells to vaporise the water content of the tissue. As a result of this increasing desiccation, particularly adjacent to the RF emitting region of the instrument (referred to herein as an RF blade) which has the highest current density of the entire current path through tissue, the tissue adjacent to the cut pole of the RF blade loses direct contact with the blade. The applied voltage then appears almost entirely across this void which ionises as a result, forming a plasma, which has a very high volume resistivity compared to tissue. This differentiation is important as it focuses the applied energy to the plasma that completed the electrical circuit between the cut pole of the RF blade and the tissue. Any volatile material entering the plasma slowly enough is vaporised and the perception is therefore of a tissue dissecting plasma.

GB 2 486 343 discloses a control system for an electrosurgical apparatus which delivers both RF and microwave energy to treat biological tissue. The energy delivery profile of both RF energy and microwave energy delivered to a probe is set based on sampled voltage and current information of RF energy conveyed to the probe and sampled forward and reflected power information for the microwave energy conveyed to and from the probe.

GB 2 522 533 discloses an isolating circuit for an electrosurgical generator arranged to produce radiofrequency (RF) energy and microwave energy for treating biological tissue. The isolating circuit comprises a tunable waveguide isolator at a junction between the microwave channel and signal combiner, and can include a capacitive structure between a ground conductor of the signal combiner and a conductive input section of the waveguide isolator to inhibit coupling of the RF energy and leakage of the microwave energy.

SUMMARY OF THE INVENTION

At its most general, the present invention provides a combined isolator-diplexer device for supplying radiofrequency (RF) electromagnetic (EM) energy and microwave EM energy obtained from separate source to a probe via a common signal pathway. The invention combines into a single unit all the necessary components to isolate the microwave and RF channels from one another whilst providing a high withstanding voltage (e.g. greater than 10 kV).

The invention improves upon the structure disclosed in GB 2 522 533 by providing the necessary isolation with a plurality of series-connected capacitive structure integrally formed with a waveguide isolator that assists in reducing capacitive coupling across the isolation barrier.

According to the invention, there is provided a combined isolator-diplexer device comprising: a combining circuit having a first input connectable to receive radiofrequency (RF) electromagnetic (EM) radiation having a first frequency from an RF channel, a second input connectable to receive microwave EM radiation having a second frequency that is higher than the first frequency from a microwave channel, and an output in communication with the first and second inputs for conveying the RF EM radiation and the microwave EM radiation to a common signal pathway, and a waveguide isolator connected to isolate the microwave channel from the RF EM radiation, wherein the waveguide isolator comprises: a conductive input section, a conductive output section, a conductive intermediate section, the intermediate section having a first end which mates with the input section, and a second end which mates with the output section, a first DC isolation barrier arranged between the input section and the intermediate section, and a second DC isolation barrier arranged between the intermediate section and the output section, wherein the input section, intermediate section and output section together enclose a waveguide cavity, wherein the output from the combining circuit includes a signal conductor and a ground conductor, and wherein the first DC isolation barrier and the second DC isolation barrier provide a pair of series-connected capacitive structures between the ground conductor of the output from the combining circuit and the conductive input section of the waveguide isolator, the capacitive structure being arranged to inhibit coupling of the RF EM energy and leakage of the microwave EM energy.

By providing a plurality (preferably a pair) of capacitive elements connected in series within the structure of the waveguide isolator itself, the overall capacitance can be reduced without disturbing the transmission of microwaves to the output or allowing unacceptable level of microwave radiation or leakage.

The input section, intermediate section and output section may be disposed in sequence along a longitudinal direction, wherein the intermediate section overlaps in the with the input section in the longitudinal direction at the first DC isolation barrier, and wherein the intermediate section overlaps in the with the output section in the longitudinal direction at the second DC isolation barrier. These regions of overlap provide two capacitive sections. The intermediate section is arranged to ensure that the two capacitive sections are spaced apart at or around a multiple of a half guide-wavelength at the microwave frequency in the intermediate section so that reflection of microwave energy due to the change in diameter at the joints between sections is cancelled. The extent of the longitudinal overlap between the intermediate section and the input and output sections respectively may be restricted by a pair of spacer elements. The may be a first spacer element mounted between the intermediate section and the input section and a second spacer element mounted between the intermediate section and the output section. The spacers may be mounted within recesses formed in the input section and output section, such that they abut a facing edge of the intermediate section. The spacer elements may be formed from an insulating plastic, such as Delrin® or polyvinylchloride (PVC). If the waveguide is cylindrical, the spacer elements may each comprise an annular sleeve mounted over the distal end of one of the input or output sections of the waveguide isolator. The outer surface of the sleeves may be flush with the outer surface of the input and output sections.

The longitudinal length of the overlap between the inner section and outer section and the respective portions of the intermediate section is preferably at or around an odd number of quarter wavelengths (usually one quarter wavelength) at the microwave frequency.

An insulating layer may be disposed in each overlapping region, i.e. between the input section and the intermediate section at the first DC isolation barrier, and between the output section and the intermediate section at the second DC isolation barrier. A common insulating layer may be provided, i.e. one insulating layer may extend between the overlapping regions, e.g. under or through the intermediate section.

The insulating layer may have a thickness (e.g. radial thickness if the waveguide is cylindrical) that is selected to be either as thin as possible to minimise microwave leakage. By providing a pair of capacitive structures, this layer can be made thinner without increasing the capacitance to unwanted levels.

The output connected to the common signal pathway may includes an output probe mounted on the output section of the waveguide isolator. The output probe may have a first coupling conductor extending into the waveguide isolator to couple the microwave EM energy therefrom. Similarly, the second input may include an input probe mounted on the input section of the waveguide isolator. The input probe may have a second coupling conductor extending into the waveguide isolator to couple the microwave EM energy into the cavity. The first coupling conductor and second coupling conductor may extend in a direction that is orthogonal to the longitudinal direction. In one example, the first coupling conductor and second coupling conductor may extend into the waveguide cavity from opposite directions.

The first input may include an RF connector mounted on the waveguide isolator. The RF connector may have a signal conductor that extends into the waveguide cavity to electrically contact the coupling conductor of the output probe. The signal conductor may extend in the longitudinal direction, and may be positioned to substantially align with an equipotential of the microwave EM energy within the waveguide isolator. Aligning the signal conductor in this way means that the amount of microwave EM energy that can leak into the RF connector is minimal.

However, as a further barrier to leakage, the RF connector may comprise a coaxial filter connected to the output section and configured to inhibit microwave EM energy from leaking out of the waveguide isolator through the signal conductor of the RF connector. The coaxial filter may comprise a two section re-entrant coaxial filter.

The waveguide isolator may comprise an adjustable impedance. For example, it may comprise a plurality of tuning stubs that are adjustably insertable into the waveguide cavity along the longitudinal direction. The plurality of tuning stubs may comprise a first tuning stub insertable through an end face of the input section, and a second tuning stub insertable through an end face of the output section. If the waveguide cavity is cylindrical, the tuning stubs may lie on the axis of the cylinder.

In another aspect, the invention may provide an electrosurgical apparatus for resection of biological tissue, the apparatus comprising: a radiofrequency (RF) signal generator for generating RF electromagnetic (EM) radiation having a first frequency; a microwave signal generator for generating microwave EM radiation having a second frequency that is higher than the first frequency; a probe arranged to deliver the RF EM radiation and the microwave EM radiation separately or simultaneously from a distal end thereof; and a feed structure for conveying the RF EM radiation and the microwave EM radiation to the probe, the feed structure comprising an RF channel for connecting the probe to the RF signal generator, and a microwave channel for connecting the probe to the microwave signal generator, wherein the RF channel and microwave channel comprise physically separate signal pathways from the RF signal generator and microwave signal generator respectively, wherein the feed structure includes an isolator-diplexer device comprising: a combining circuit having a first input connected to receive the RF EM radiation from the RF channel, a second input connected to receive the microwave EM radiation from the microwave channel, and an output in communication with the first and second inputs for conveying the RF EM radiation and the microwave EM radiation to the probe along a common signal pathway, and a waveguide isolator connected to isolate the microwave channel from the RF EM radiation, wherein the waveguide isolator comprises: a conductive input section, a conductive output section, a conductive intermediate section, the intermediate section having a first end which mates with the input section, and a second end which mates with the output section, a first DC isolation barrier arranged between the input section and the intermediate section, and a second DC isolation barrier arranged between the intermediate section and the output section, wherein the input section, intermediate section and output section together enclose a waveguide cavity, wherein the output from the combining circuit includes a signal conductor and a ground conductor, and wherein the first DC isolation barrier and the second DC isolation barrier provide a pair of series-connected capacitive structures between the ground conductor of the output from the combining circuit and the conductive input section of the waveguide isolator, the capacitive structure being arranged to inhibit coupling of the RF EM energy and leakage of the microwave EM energy.

This aspect of the invention may be combined with any or all of the components (either individually or in any combination) described below with reference to the electrosurgical apparatus 400 of FIG. 1. For example, the RF channel and microwave channel may include any or all of the components of the RF channel and microwave channel respectively described below. The microwave channel may include a circulator for separating a reflected signal on the microwave channel from a forward signal. In an alternative embodiment, a directional coupler may be used for the same purpose. In practice, the circulator or directional coupler will exhibit imperfect isolation, which in turn affects the reflected signal that is actually received at the detector. The isolator-diplexer device may comprise an adjustable impedance capable of compensating for this imperfect isolation as well as optimising return loss and transmission in the waveguide isolator.

The apparatus may be configured to supply energy for cutting and coagulating tissue simultaneously (e.g. a mixed or blend mode) or may be operated independently, whereby the RF and microwave energy is delivered to the probe under manual user control (e.g. based on the operation of a footswitch pedal) or automatically based on measured phase and/or magnitude information from the RF and/or microwave channel. The system may be used to perform tissue ablation and cutting. In the instance where microwave and RF energy are delivered simultaneously, either or both RF and microwave energy returned to the respective generators may be used at high power or low power to control the energy delivery profile. In this instance, it may be desirable to take measurements during the OFF time when the energy delivery format is pulsed.

The distal end of the probe may comprise a bipolar emitting structure comprising a first conductor spatially separated from a second conductor, the first and second conductors being arranged to act: as active and return electrodes respectively to convey the RF EM radiation by conduction, and as an antenna or transformer to facilitate radiation of the microwave EM energy. Thus, the system may be arranged to provide a local return path for RF energy. For example, the RF energy may pass by conduction through the tissue separating the conductors, or a plasma may be generated in the vicinity of the conductors to provide the local return path. RF tissue cutting may be produced by a fixed dielectric material separating the first and second conductors, where the thickness of the dielectric material is small, i.e. less than 1 mm and the dielectric constant high, i.e. greater than that of air.

The invention may be particularly suitable in gastrointestinal (GI) procedures, e.g. to remove polyps on the bowel, i.e. for endoscopic sub-mucosal resection. The invention may also lend itself to precision endoscopic procedures, i.e. precision endoscopic resection, and may be used in ear, nose and throat procedures and liver resection.

The term "conductive" is used herein to mean electrically conductive, unless the context dictates otherwise.

The first frequency may be a stable fixed frequency in the range 10 kHz to 300 MHz and the second frequency may be a stable fixed frequency in the range 300 MHz to 100 GHz.

The first frequency should be high enough to prevent the energy from causing nerve stimulation and low enough to prevent the energy from causing tissue blanching or unnecessary thermal margin or damage to the tissue structure. Preferred spot frequencies for the first frequency include any one or more of: 100 kHz, 250 kHz, 400 kHz, 500 kHz, 1 MHz, 5 MHz. Preferred spot frequencies for the second frequency include 915 MHz, 2.45 GHz, 5.8 GHz, 14.5 GHz, 24 GHz. Preferably the second frequency is at least an order of magnitude (i.e. at least 10 times) higher than the first frequency.

BRIEF DESCRIPTION OF THE DRAWINGS

Embodiments of the invention are described in detail below with reference to the accompanying drawings, in which.

DETAILED DESCRIPTION; FURTHER OPTIONS AND PREFERENCES

Background

Figure 1:
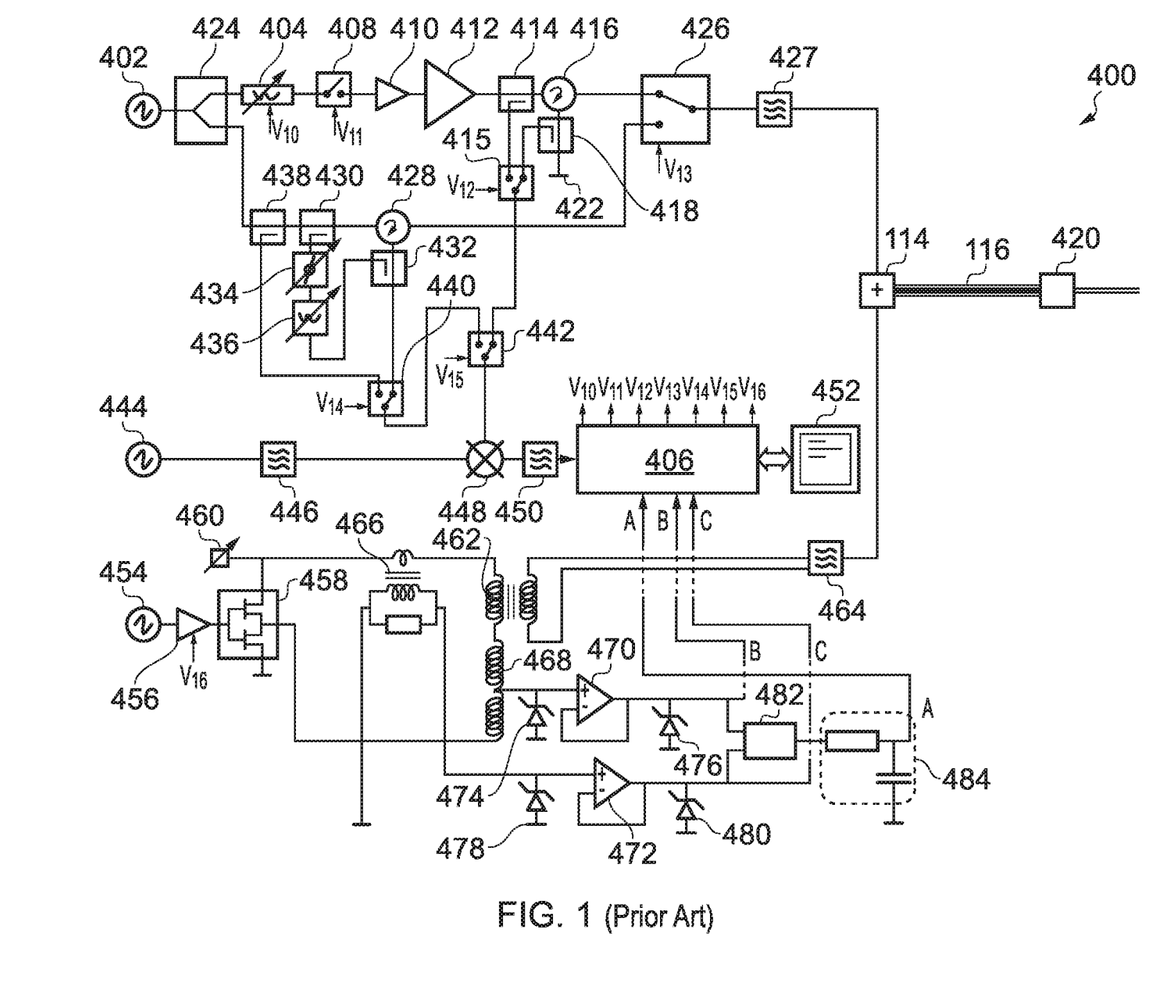
FIG. 1 is an overall schematic system diagram of an electrosurgical apparatus in which the present invention may be used.

FIG. 1 shows a schematic diagram of an electrosurgical apparatus 400 such as that disclosed in GB 2 486 343 that is useful for understanding the invention. The apparatus comprises a RF channel and a microwave channel. The RF channel contains components for generating and controlling an RF frequency electromagnetic signal at a power level suitable for treating (e.g. cutting or desiccating) biological tissue. The microwave channel contains components for generating and controlling a microwave frequency electromagnetic signal at a power level suitable for treating (e.g. coagulating or ablating) biological tissue.

The microwave channel has a microwave frequency source 402 followed by a power splitter 424 (e.g. a 3 dB power splitter), which divides the signal from the source 402 into two branches. One branch from the power splitter 424 forms a microwave channel, which has a power control module comprising a variable attenuator 404 controlled by controller 406 via control signal $V_{10}$ and a signal modulator 408 controlled by controller 406 via control signal $V_{11}$, and an amplifier module comprising drive amplifier 410 and power amplifier 412 for generating forward microwave EM radiation for delivery from a probe 420 at a power level suitable for treatment. After the amplifier module, the microwave channel continues with a microwave signal coupling module (which forms part of a microwave signal detector) comprising a circulator 416 connected to deliver microwave EM energy from the source to the probe along a path between its first and second ports, a forward coupler 414 at the first port of the circulator 416, and a reflected coupler 418 at the third port of the circulator 416. After passing through the reflected coupler, the microwave EM energy from the third port is absorbed in a power dump load 422. The microwave signal coupling module also includes a switch 415 operated by the controller 406 via control signal $V_{12}$ for connecting either the forward coupled signal or the reflected coupled signal to a heterodyne receiver for detection.

The other branch from the power splitter 424 forms a measurement channel. The measurement channel bypasses the amplifying line-up on the microwave channel, and hence is arranged to deliver a low power signal from the probe. A primary channel selection switch 426 controlled by the controller 406 via control signal $V_{13}$ is operable to select a signal from either the microwave channel or the measurement channel to deliver to the probe. A high band pass filter 427 is connected between the primary channel selection switch 426 and the probe 420 to protect the microwave signal generator from low frequency RF signals.

The measurement channel includes components arranged to detect the phase and magnitude of power reflected from the probe, which may yield information about the material e.g. biological tissue present at the distal end of the probe. The measurement channel comprises a circulator 428 connected to deliver microwave EM energy from the source 402 to the probe along a path between its first and second ports. A reflected signal returned from the probe is directed into the third port of the circulator 428. The circulator 428 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit may be used that injects a portion of the forward signal (from forward coupler 430) back into the signal coming out of the third port (via injection coupler 432). The carrier cancellation circuit include a phase adjustor 434 to ensure that the injected portion is 180° out of phase with any signal that breaks through into the third port from the first port in order to cancel it out. The carrier cancellation circuit also include a signal attenuator 436 to ensure that the magnitude of the injected portion is the same as any breakthrough signal.

To compensate for any drift in the forward signal, a forward coupler 438 is provided on the measurement channel. The coupled output of the forward coupler 438 and the reflected signal from the third port of the circulator 428 are connected to respective input terminal of a switch 440, which is operated by the controller 406 via control signal $V_{14}$ to connect either the coupled forward signal or the reflected signal to a heterodyne receiver for detection.

The output of the switch 440 (i.e. the output from the measurement channel) and the output of the switch 415 (i.e. the output from the microwave channel) are connect to a respective input terminal of a secondary channel selection switch 442, which is operable by the controller 406 via control signal $V_{15}$ in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 442. A single heterodyne receiver is shown in this system, but a double heterodyne receiver (containing two local oscillators and mixers) to mix the source frequency down twice before the signal enters the controller may be used if necessary. The heterodyne receiver comprises a local oscillator 444 and a mixer 448 for mixing down the signal output by the secondary channel selection switch 442. The frequency of the local oscillator signal is selected so that the output from the mixer 448 is at an intermediate frequency suitable to be received in the controller 406. Band pass filters 446, 450 are provided to protect the local oscillator 444 and the controller 406 from the high frequency microwave signals.

The controller 406 receives the output of the heterodyne receiver and determines (e.g. extracts) from it information indicative of phase and magnitude of the forward and/or reflected signals on the microwave or measurement channel. This information can be used to control the delivery of high power microwave EM radiation on the microwave channel or high power RF EM radiation on the RF channel. A user may interact with the controller 406 via a user interface 452, as discussed above.

The RF channel shown in FIG. 1 comprises an RF frequency source 454 connected to a gate driver 456 that is controlled by the controller 406 via control signal $V_{16}$. The gate driver 456 supplies an operation signal for an RF amplifier 458, which is a half-bridge arrangement. The drain voltage of the half-bridge arrangement is controllable via a variable DC supply 460. An output transformer 462 transfers the generated RF signal on to a line for delivery to the probe 420. A low pass, band pass, band stop or notch filter 464 is connected on that line to protect the RF signal generator from high frequency microwave signals.

A current transformer 466 is connected on the RF channel to measure the current delivered to the tissue load. A potential divider 468 (which may be tapped off the output transformer) is used to measure the voltage. The output signals from the potential divider 468 and current transformer 466 (i.e. voltage outputs indicative of voltage and current) are connected directly to the controller 406 after conditioning by respective buffer amplifiers 470, 472 and voltage clamping Zener diodes 474, 476, 478, 480 (shown as signals B and C in FIG. 1).

To derive phase information, the voltage and current signals (B and C) are also connected to a phase comparator 482 (e.g. an EXOR gate) whose output voltage is integrated by RC circuit 484 to produce a voltage output (shown as A in FIG. 1) that is proportional to the phase difference between the voltage and current waveforms. This voltage output (signal A) is connected directly to the controller 406.

The microwave/measurement channel and RF channel are connected to a signal combiner 114, which conveys both types of signal separately or simultaneously along cable assembly 116 to the probe 420, from which it is delivered (e.g. radiated) into the biological tissue of a patient.

A waveguide isolator (not shown) may be provided at the junction between the microwave channel and signal combiner.

The waveguide isolator may be configured to perform three functions: (i) permit the passage of very high microwave power (e.g. greater than 10 W); (ii) block the passage of RF power; and (iii) provide a high withstanding voltage (e.g. greater than 10 kV). A capacitive structure (also known as a DC break) may also be provided at (e.g. within) or adjacent the waveguide isolator. The purpose of the capacitive structure is to reduce capacitive coupling across the isolation barrier.

Figure 2:
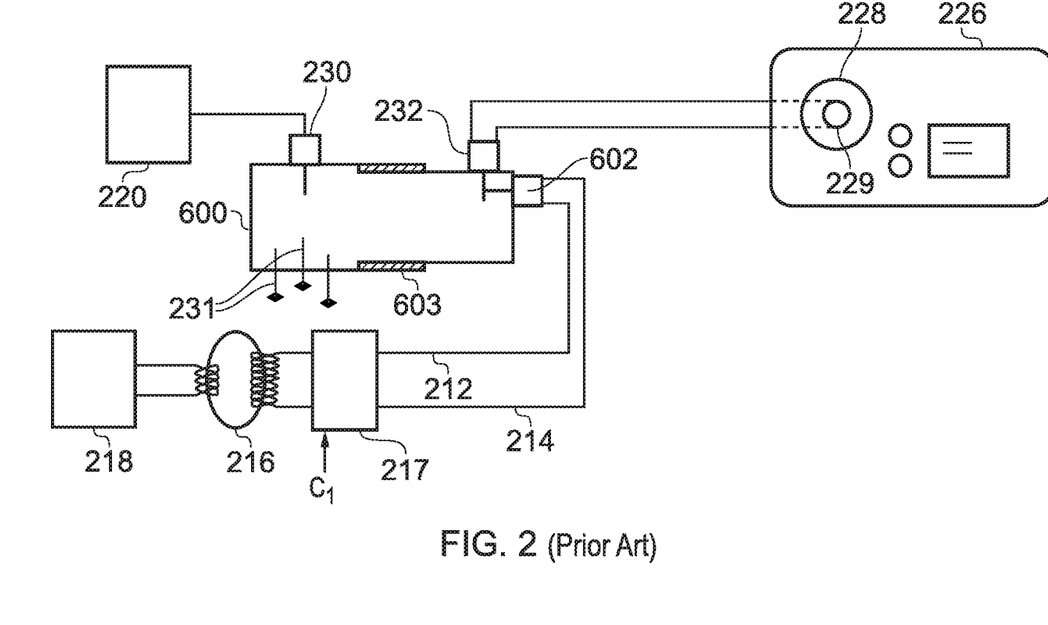
FIG. 2 is a schematic diagram of a known example of an isolating circuit that can be used in an electrosurgical apparatus.

FIG. 2 is a schematic diagram of an isolating circuit as disclosed GB 2 522 533, which is also useful for understanding the invention. The isolating circuit forms part of a feed structure for conveying RF EM radiation from an RF signal generator 218 and microwave radiation from a microwave signal generator 220 to a probe. The probe (not shown) is connectable to an output port 228 provided in a housing 226. An insulating sleeve 229 is provided at the output port 228 of the housing to prevent a current path for connecting the grounded casing of the housing with the floating components connected to the output port 228.

The feed structure comprises an RF channel having a RF signal pathway 212, 214 for conveying the RF EM radiation and a microwave channel having a microwave signal pathway 210 for conveying the microwave EM radiation. The signal pathways for the RF EM radiation and microwave radiation are physically separate from each other. The RF signal generator is connected to the RF signal pathway 212, 214 via a voltage transformer 216. The secondary coil of the transformer 216 (i.e. on the probe side of the arrangement) is floating, so there is not direct current path between the patient and the RF signal generator 218. This means that both the signal conductor 212 and ground conductor 214 of the RF signal pathway 212, 214 are floating.

The isolating circuit comprises a waveguide isolator 600 whose insulating gap is configured to provide the necessary level of DC isolation whilst also having a capacitive reactance that is low enough at the frequency of the microwave energy to prevent leakage of the microwave energy at the gap. The gap may be 0.6 mm or more, e.g. 0.75 mm. RF energy is not able to couple between the two ends of the isolator because the diameter of the tube creates a very large inductance in series with each of the probes at the RF frequency.

The isolating circuit has a combining circuit integrated with the waveguide isolator 600. A signal conductor 212 and ground conductor 214 carrying the RF signal are connected to a coaxial RF connector 602 (RF feed), which introduces the RF signal into the waveguide isolator 600, from where it is conveyed out from an output port 232 towards the probe.

The isolating gap 603 is arranged to prevent the RF signal from coupling back into the input port 230. Microwave energy is prevented from coupling into the RF connector 602 by careful placement of the inner conductive rod within the waveguide isolator.

A tuning unit is incorporated into the waveguide isolator 600 in order to reduce the return loss of the line up of components. The tuning unit comprises three stubs 231 that can be adjustably inserted, e.g. screwed, into the body of the cavity.

In addition, the RF channel has an adjustable reactance 217 that is operable under the control of control signal Ci to accommodate (e.g. compensate for) changes in capacitance arising from different lengths of cable used with the generator. The adjustable reactance 217 may comprise one or more of switched or electronically tunable capacitors or inductors connected in shunt or series with the RF channel.

Enhanced Combined Isolator-Diplexer

The present invention provides a combined isolator-diplexer that improves upon the isolating circuit discussed above with reference to FIG. 2. Embodiments of the invention may provide a combined isolator-diplexer suitable for use with an electrosurgical generator that generates RF waveforms and microwave waveforms at widely different frequencies, e.g. at 5.8 GHz and 400 kHz, to enable an electrosurgical instrument to provide different forms of treatment using energy received from a common supply line.

An embodiment of a combined isolator-diplexer is described below with reference to FIGS. 3 to 5. Aspects of its performance, obtained by simulation (e.g. using CST simulation software), are then described with reference to FIGS. 6 to 9.

The combined isolator-diplexer operates to prevent high voltage RF from reaching the microwave source, where it may cause damage, and to prevent microwave power from traveling along the cable to the RF source, where it would radiate. In each case leakage would also result in wastage of generated power, which should be avoided.

The combined isolator-diplexer provides a waveguide isolator having a DC break in both the inner and outer conductors that connect the microwave source to the probe. The DC break operates to prevent high voltage RF reaching the microwave source, without disturbing the transmission of microwaves to the probe or allowing radiation of microwaves through the DC break.

Where a waveguide isolator is used alone, a capacitance of the DC break in the outer conductor may be too high for efficient operation. This problem is addressed by provided a coaxial isolator in addition to or integrated within the waveguide isolator to effectively connect a series capacitance to the outer conductor without impeding the transmission of microwaves or allowing radiation.

Figure 3:
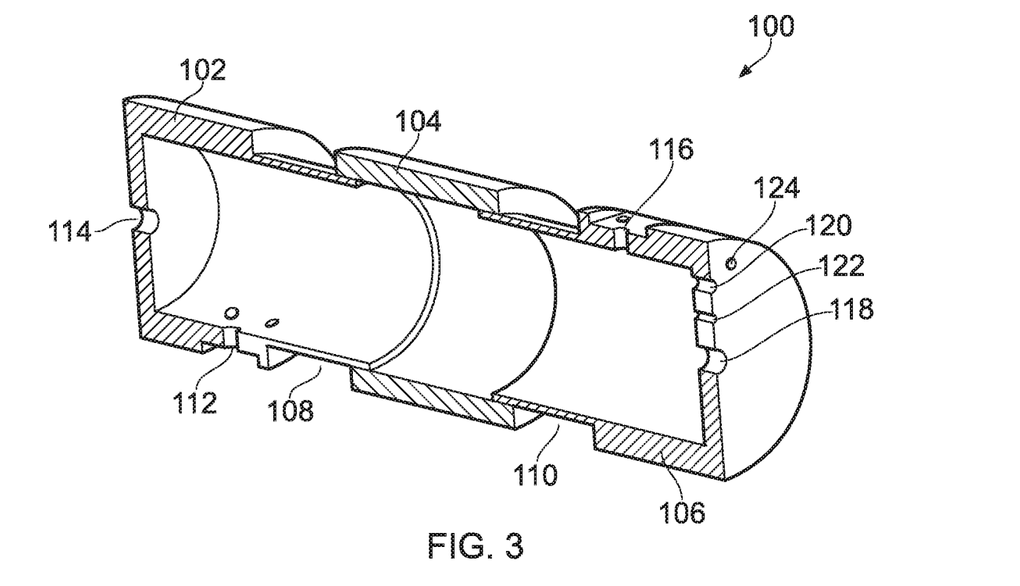
FIG. 3 is a schematic cut-away illustration of the conductive components of a combined isolator-diplexer that is an embodiment of the invention.
Figure 4:
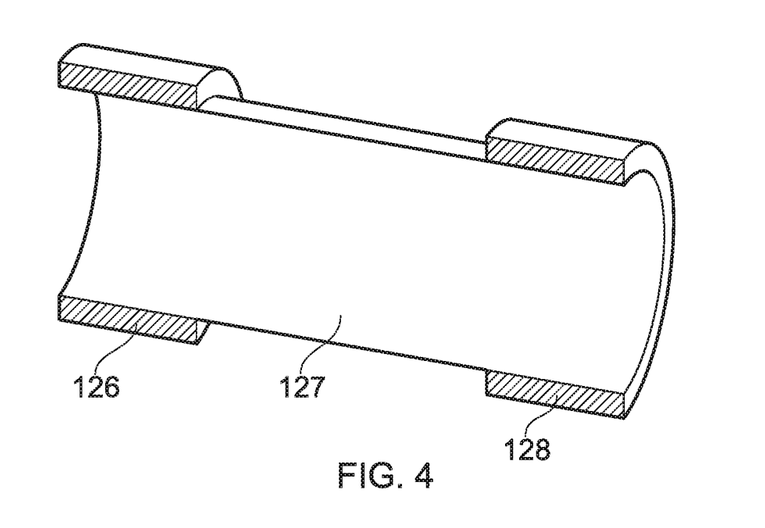
FIG. 4 is a schematic cut-away illustration of the insulating components in the combined isolator-diplexer that is an embodiment of the invention.

FIG. 3 is a schematic cut-away view of a combined isolator-diplexer 100 that is an embodiment of the invention. The combined isolator-diplexer comprising a cylindrical waveguide isolator along a longitudinal axis of In FIG. 3 only the electrically conductive elements of the isolator are depicted.

The cylindrical waveguide isolator of the combined isolator-diplexer 100 is formed from a pair of end caps 102, 106 separated by collar 104.

The waveguide isolator has an input end formed by an input end cap 102 that is arranged to receiving an microwave feed at an input port 112. The input port 112 is arranged on a circumferential side wall of the input end cap 102. The input port 112 is adapted to receive a coaxial cable, and comprising a passageway through the circumferential wall of the end cap to allow an inner conductor of a connected coaxial cable (not shown) to extend radially into the cylindrical space defined by the waveguide isolator. The cylindrical space may be filled with insulating dielectric material (e.g. air).

The waveguide isolator has an output end formed by an output end cap 106 that is connectable to an output line via an output port 116. The output port 116 is arranged on a circumferential side wall of the output end cap 106. The output port 116 is adapted to receive a coaxial cable, and comprising a passageway through the circumferential wall of the end cap to allow an inner conductor of a connected coaxial cable (not shown) to extend radially into the cylindrical space defined by the waveguide isolator. As discussed in more detail below, the inner conductor may form part of an RF diplexer structure for transferring an RF signal into the coaxial cable that is connected to output port 116. The inner conductors of the coaxial cables that protrude into the cylindrical waveguide cavity are thus insulated from each other by the dielectric material in the cavity.

In this example, the input port 112 and the output port 116 are on opposing sides of the cylinder formed by the waveguide. This may be useful to fit with connections to other components, but it is not essential. In the simulations discussed below, for example, the input port and output port are on the same side of the cylinder.

The input end cap 102 and the output end cap 106 are cylindrical elements having one closed axial end and one open axial end. The end caps 102, 106 are disposed with there axes aligned and with their open axial ends facing one another. The input end cap 102 is configured to be in electrical communication with an outer conductor of a coaxial cable connected to the input port 112. The output end cap 106 is configured to be in electrical communication with an outer conductor of a coaxial cable connected to the output port 116. The end caps 102, 106 are physically separated from each other along the axis of the cylinder. The separation in maintained by an electrically conductive collar 104 and a pair of insulating spacers 126, 128 (see FIG. 4) which are respectively seated in a corresponding circumferential recess 108, 110 formed at the open end of the input end cap 102 and output end cap 106.

The collar 104 overlies the axial gap between the open axial ends of the end caps 102, 106 in order to complete the cylindrical waveguide cavity. In order to insulate the end caps from each other (and therefore to isolate the outer conductors of the coaxial cables that are connected thereto), an insulating layer 127 (see FIG. 4) is disposed around the outer surfaces of a distal portion of both end caps in order to provide a dielectric (electrically insulating) barrier in a circumferential gap between the outer surfaces of the end caps 102, 106 and the inner surface of the collar 104 in a region where they overlap.

With this arranged, the waveguide isolator comprises two insulating portions arranged in series along the axis of the cylinder. A first insulating portion occurs at the overlap between the input end cap 102 and the collar 104. A second insulating portion occurs at the overlap between the output end cap 106 and the collar 104. With this structure, the capacitance between the two end caps can be reduced, so that the capacitance of the structure is less than seen with just one insulating portion. The reduction in capacitance does not lead to a meaningful increase in microwave leakage because most power coupled from the guide is reflected because the sharp corners at the ends of the cavity create a high impedance to the passage of the wave.

The insulating layer 127 may be provided by any suitable material. In one example, the insulating layer 127 may comprise a plurality (e.g. 2, 3, or more) turns of Kapton® film. The film material may have a dielectric constant of 3.4 and a dissipation factor of 0.002. The film may have a thickness of 0.005 mm, and a plurality of turns may be used to provide the insulating layer with an appropriate thickness.

In other examples, the insulating layer may be a tubular element, e.g. similar to a washer, that sits between the end caps 102, 106 and the collar 104. Because the two insulating gaps are in series, either of which can withstand the required voltage, the presence of one pinhole in the insulator will not cause a breakdown of insulation. For this reason the insulator may be either a coiled (wrapped) dielectric sheet with multiple layers or a tube, with one layer.

The insulating spacers 126, 128 may each comprise rigid insulating rings, e.g. made of Delrin® plastic or polyvinylchloride (PVC). The spacers may have an axial length selected to define the correct length for the overlap regions (each of which can be considered as a separate choke).

As mentioned above, the insulating layer 127 is located in a circumferential gap between the outer surfaces of the end caps 102, 106 and the inner surface of the collar 104 in a region where they overlap. The gap may have a mean diameter of 41.05 mm and a radial thickness of 0.15 mm. The capacitance of each gap, which may be partially or completely filled with the dielectric material of the insulating layer 127, may be around 110 pF. This means that the two gaps in series provide a capacitance of about 55 pF.

Each of the end caps 102, 106 has a through hole formed in its closed axial end. The through holes may be arranged symmetrically with each other with respect to the axis of the cylinder. In this example, the through holes are on the axis of the cylinder. Thus, input end cap 102 has a through hole 114 formed centrally in its closed axial end. The output end cap 106 has a through holes 118 formed centrally in its closed axial end. The through holes 114, 118 are arranged to receive electrically conductive pin or screw elements, which are selectively and controllably insertable into the cavity to enable tuning, i.e. to enable optimisation of the insertion loss and return loss of the combined isolator-diplexer.

In the example shown in FIG. 3, the output end cap comprises three additional holes 120, 122, 124. These holes are relating to the diplexer function, which is shown in more detail in FIG. 5.

Figure 5:
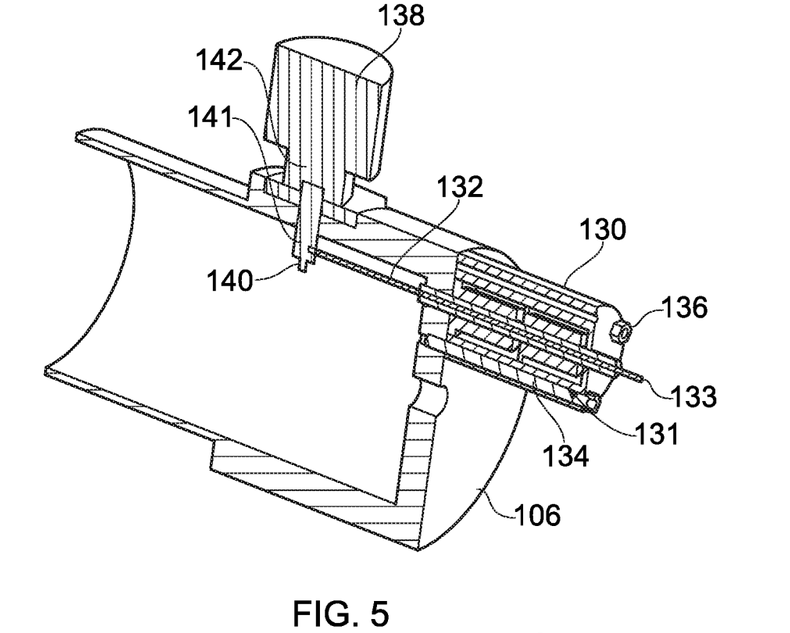
FIG. 5 is schematic cut-away illustration of an RF diplexer configuration for the combined isolator-diplexer that is an embodiment of the invention.

FIG. 5 shows a cut-away view of the output end cap 106. A coaxial cable 142 is connected to the output port 116 using a suitable connector 138. An inner conductor 140 of the coaxial cable 142 protrudes into the cavity. The inner conductor 140 is still surrounded by the dielectric material 141 from the coaxial cable for a portion of the length that it extends into the cavity.

The diplexer functionality of the device is provided by introducing a RF connection element 132 perpendicularly through a hole 120 in the closed end face of the output end cap 106. The hole 120 is directly in line with the inner conductor 140 of the output coaxial cable, so that it makes contact with the inner conductor 140 part of the way down its length. If the RF connection element 132 is inserted so as to make contact at the right distance down the centre conductor then no microwave power is coupled to the RF connection element 132. This connection affects slightly a match to the microwave connector but a good match for the microwave energy can be recovered by making changes to the length of the inner conductor 140.

The RF connection line 132 is connected to the output end cap 106 by a connector body 130, which is secured to the output end cap 106 by pair of screws 134, 136 that are respectively received in a pair of holes 122, 124 formed in the closed end face of the output end cap 106. The connector body 130 comprises a microwave filter 131 for blocking microwave energy. In this example, the microwave filter 131 is a cylindrical coaxial filter connected to the end of the output end cap. The cylindrical coaxial filter may be a two section re-entrant coaxial filter, e.g. designed to strongly reject frequencies at and around 5.8 GHz. The microwave filter 131 is placed at such a distance from the inside end wall of the output end cap 106 so that, at microwave frequencies, the RF connection element 132 appears to be short-circuited to the end wall, to prevent microwave energy from exiting via the RF connection element 132.

The RF signal (e.g. from input lines 212, 214 as shown in FIG. 2) is applied between a distal end 133 of the RF connection element 132, and the electrically conductive body 130 of the filter, which in turn is electrically connected to the outer surface of the output end cap 106. The connection of the RF signal could be by a standard coaxial connector if convenient.

The RF connection element 132 extends to touch the inner conductor 140 of the output coaxial cable (which may take the form of a microwave connector). The RF connection element 132 may be soldered to the inner conductor 140.

The RF connection element 132 is insulated from the output section and from the other conductive filter parts by an insulating tube 146 (see FIG. 8), e.g. made from PTFE or the like. The RF connection element 132 may be a rigid pin structure. In one example, the RF connection element 132 and the insulating tube 146 may be constructed by stripping the outer copper jacket from a short length of semi-rigid coaxial cable.

Figure 6:
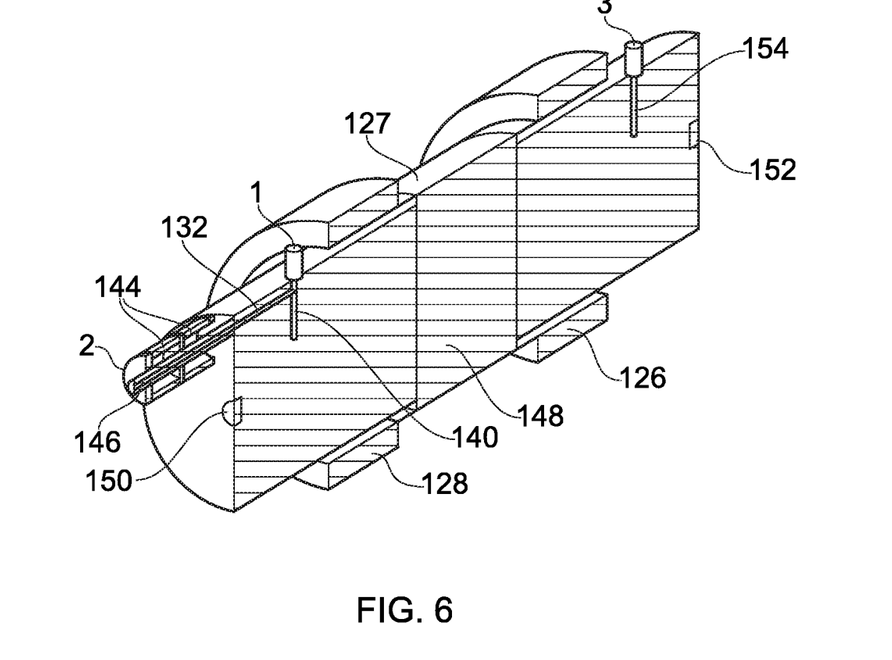
FIG. 6 is a cut-away diagram of a simulation model of the combined isolator-diplexer that is an embodiment of the invention.

FIG. 6 is a cut-away diagram of a simulation model of the combined isolator-diplexer that is an embodiment of the invention. Feature already described are given the same reference number and are not discussed again. For clarity, with the exception of the three connector pins 132, 140, 154 and two tuning elements 150, 152, FIG. 6 shows only the dielectric (i.e. electrically insulating) components of the combined isolator-diplexer. These dielectric components include air 148 inside the waveguide cavity and air 144 inside the microwave filter. They also include the dielectric spacers 126, 128 and insulating layer 127 discussed above. The simulation was run on the basis that the conductive components discussed above with reference to FIGS. 3 and 5 were also present.

There are three ports on the device. Port 1 is the combined RF/microwave output port. Port 2 is the RF connection line 132, which introduces RF energy at 400 kHz. Port 3 is the microwave inlet port, which introduces microwave energy (e.g. at 5.8 GHz in the preferred example). The simulation was carried out with both microwave ports (port 1 and port 3) on the same side of the cylinder.

Figure 7:
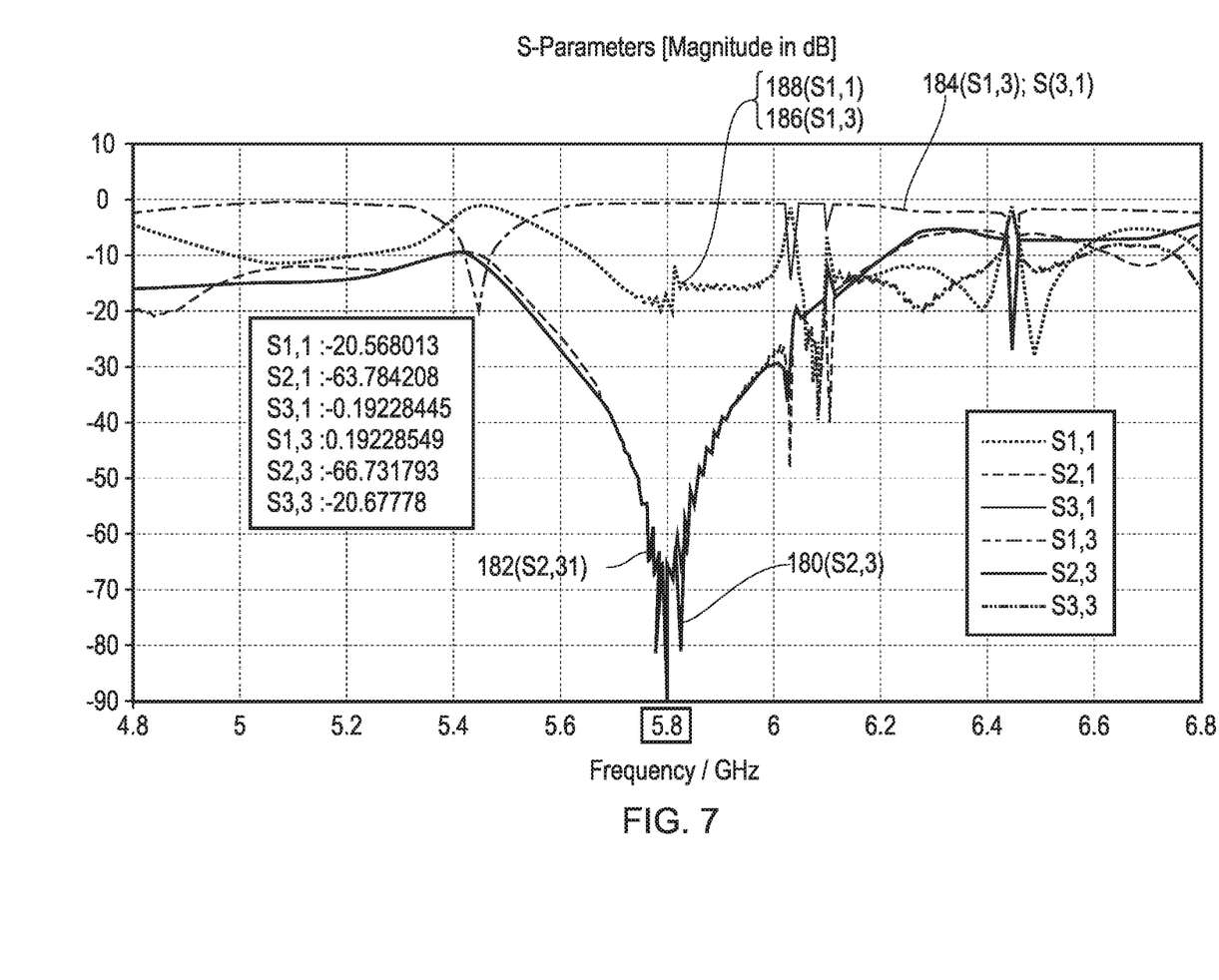
FIG. 7 is a graph showing predicted transmission and reflection parameters obtained using the simulation model of the combined isolator-diplexer that is an embodiment of the invention.

FIG. 7 is a graph showing predicted transmission and reflection parameters obtained using the simulation model of the combined isolator-diplexer of FIG. 6, between 4.8 GHz and 6.8 GHz. The inset table on the graph gives the value for each parameter at 5.8 GHz.

Lines 180, 182 show that the coupling from the input port and output port to the RF port (S21, S23) is smaller than −60 dB in a range from 5.78 GHz to 5.82 GHz.

Line 186 shows that the match at the input port (S33) is close to −20 dB at 5.8 GHz.

Line 188 shows that the match at the output port (S11) is also close to −20 dB at 5.8 GHz.

Line 184 shows that the loss between the input and output ports (S31, S13) is −0.19 dB at 5.8 GHz.

Figure 8:
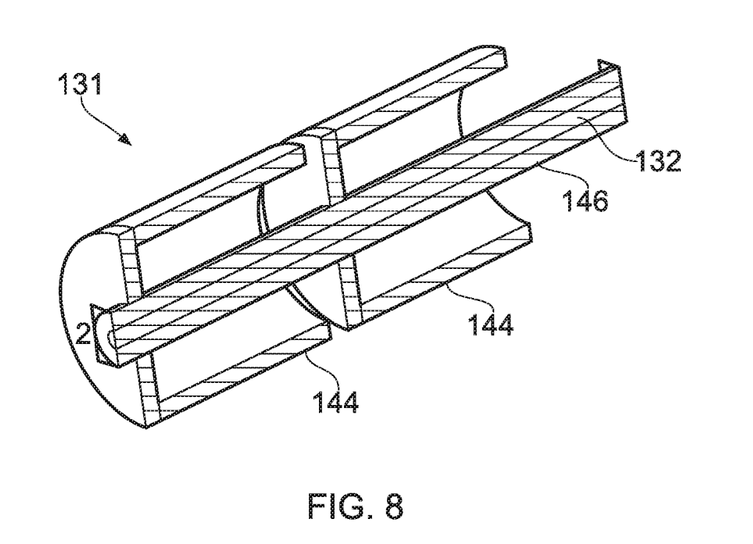
FIG. 8 is a cut-away section of a simulation model of a microwave filter mounted at an RF port of the combined isolator-diplexer that is an embodiment of the invention.

FIG. 8 is a cut-away section of a simulation model of the microwave filter 131 mounted at the RF port. The filter has a cylindrical shape. The RF connection element 132 extends along an axis of the cylinder. The RF connection element 132 is surrounded by insulating sleeve 146, e.g. made from PTFE. The filter 131 comprises an electrically conductive body 130 (omitted for clarity in FIG. 8, but shown in FIG. 3) that defines a pair of axially separated air-filled cavities 144 which act as chokes for inhibiting or prevent passage of microwave energy. At 5.8 GHz each air-filled cavity are a quarter-wave long, from the coaxial transmission line to its closed end. A quarter-wave cavity presents an open circuit in the outer conductor of the coaxial transmission line that prevent the 5.8 GHz signal from passing. The spacing of the cavities is arranged such that each reinforces the effect of the other. At 400 kHz the filter has no effect, so the RF signal input is not impeded.

Figure 9:
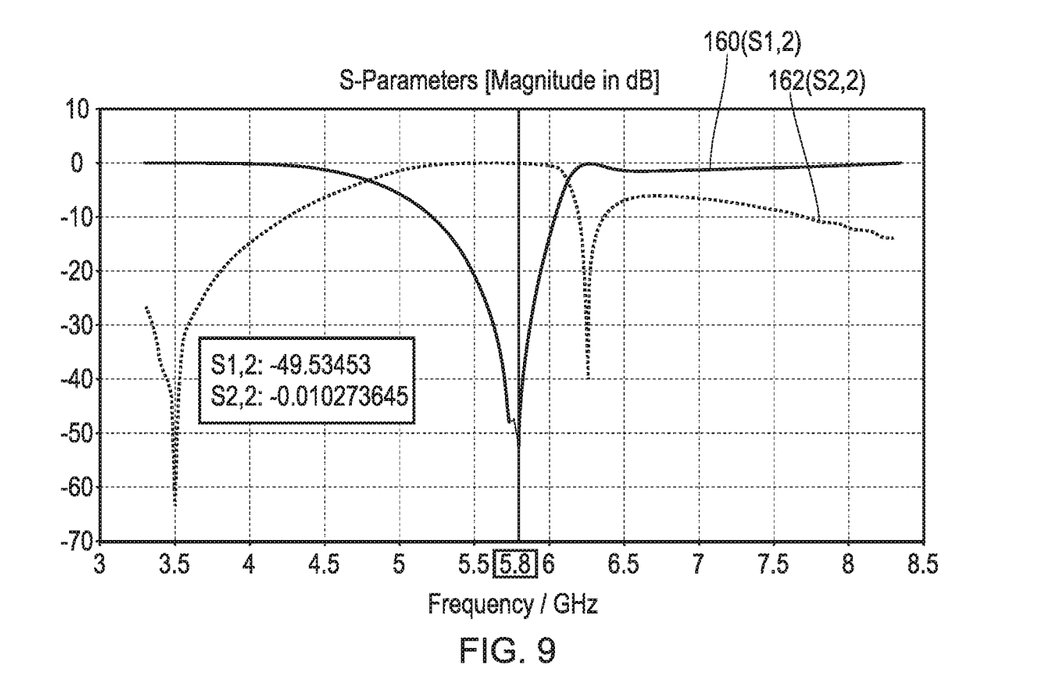
FIG. 9 is a graph showing predicted transmission and reflection parameters for the microwave filter obtained using the simulation model of FIG. 8.

FIG. 9 is a graph showing predicted transmission and reflection parameters for the microwave filter obtained using the simulation model of FIG. 8, from 3 GHz to 8.5 GHz.

Line 160 shows transmission through the filter (S12), whereas line 162 shows reflection from the filter (S22). The lines for S21 and S11 are identical to those for S12 and S22.

At 5.8 GHz the predicted insertion loss is very high (−49.5 dB), and the reflection loss very low (−0.0102 dB). This performance was with 50Ω loads at each end. In practice, there may be a higher impedance load at both ends, so that real performance will differ slightly from the simulation. For example, the shape and frequency of the dip may vary, depending on the exact position of both ends, and the insertion loss may be higher, because of the extra impedance mismatch.

The following discussion summarises results of measurements performed on a real example of the combined isolator-diplexer discussed above.

Measurements were made between port 3 (input) and port 1 (output) as described for FIG. 6, over a frequency range 5.6 GHz to 6 GHz. The measurements of interest were reflection (S33), transmission (S13), and loss at 5.8 GHz (which is the preferred frequency of microwave energy).

Coaxial cables were connected to the input port and output port using microwave connectors. In this example, the connectors were adapted versions of the Amphenol P/N 172224 component. These connectors were adapted by cutting down the dielectric such that 1 mm projected into the waveguide cavity and cutting down the protruding pins (the inner conductors mentioned above) so that they extending 20 mm from the connector flange. It is expected that a preferred length of the pins will be in region of 17.5 mm, so this technique provides over-long pins that can be trimmed as necessary.

With this set up and by adjusting the screw tuners in each end cap, a return loss of −34 dB and an insertion loss of −0.5 dB could be obtained.

The experiment was repeated with a device having the microwave ports on opposite sides of the waveguide. It was found that the behaviour was significantly different in this scenario. This implies that cut-off higher order modes play a significant part in the coupling, as the fundamental TE01 mode that can propagate in the waveguide should show no difference in coupling between connectors on the same side of the cylinder or on opposite sides. Nevertheless, with the arrange of the present invention it is still possible to tune the combined isolator-diplexer to achieve good performance.

The invention claimed is:

1. A combined isolator-diplexer device comprising:
a combining circuit having a first input connectable to receive radiofrequency (RF) electromagnetic (EM) radiation having a first frequency from an RF channel, a second input connectable to receive microwave EM radiation having a second frequency that is higher than the first frequency from a microwave channel, and an output in communication with the first and second inputs for conveying the RF EM radiation and the microwave EM radiation to a common signal pathway, and
a waveguide isolator connected to isolate the microwave channel from the RF EM radiation, wherein the waveguide isolator comprises:
  a conductive input section,
  a conductive output section,
  a conductive intermediate section, the intermediate section having a first end which mates with the input section, and a second end which mates with the output section,
  a first DC isolation barrier arranged between the input section and the intermediate section, and
  a second DC isolation barrier arranged between the intermediate section and the output section,
wherein the input section, intermediate section and output section together enclose a waveguide cavity,
wherein the output from the combining circuit includes a signal conductor and a ground conductor, and
wherein the first DC isolation barrier and the second DC isolation barrier provide a pair of series-connected capacitive structures between the ground conductor of the output from the combining circuit and the conductive input section of the waveguide isolator, the capacitive structure being arranged to inhibit coupling of the RF EM energy and leakage of the microwave EM energy.

2. A combined isolator-diplexer device according to claim 1 including an insulating layer disposed between the input section and the intermediate section at the first DC isolation barrier.

3. A combined isolator-diplexer device according to claim 1 including an insulating layer disposed between the output section and the intermediate section at the second DC isolation barrier.

4. A combined isolator-diplexer device according to claim 1, wherein the waveguide cavity is cylindrical.

5. A combined isolator-diplexer device according to claim 1, wherein the input section, intermediate section and output section are disposed in sequence along a longitudinal direction, wherein the intermediate section overlaps with the input section in the longitudinal direction at the first DC isolation barrier, and wherein the intermediate, section overlaps with the output section in the longitudinal direction at the second DC isolation barrier.

6. A combined isolator-diplexer device according to claim 5, wherein the waveguide isolator comprises a plurality of tuning stubs that are adjustably insertable into the waveguide cavity along the longitudinal direction.

7. A combined isolator-diplexer device according to claim 6, wherein the plurality of tuning stubs comprise a first tuning stub insertable through a longitudinal end face of the input section, and a second tuning stub insertable through a longitudinal end face of the output section.

8. A combined isolator-diplexer device according to claim 5, wherein:
  the output connected to common signal pathway includes an output probe mounted on the output section of the waveguide isolator, the output probe having a first coupling conductor extending into the waveguide isolator to couple the microwave EM energy therefrom,
  the second input includes an input probe mounted on the input section of the waveguide isolator, the input probe having a second coupling conductor extending into the waveguide isolator to couple the microwave EM energy into the cavity, and
  the first coupling conductor and second coupling conductor extend in a direction that is orthogonal to the longitudinal direction.

9. A combined isolator-diplexer device according to claim 8, wherein the first coupling conductor and second coupling conductor extend into the waveguide cavity from opposite directions.

10. A combined isolator-diplexer device according to claim 8, wherein the first input includes an RF connector mounted on the waveguide isolator, the RF connector having a signal conductor that extends into the waveguide cavity to electrically contact the coupling conductor of the output probe, wherein the signal conductor extends in the longitudinal direction, and wherein the signal conductor is positioned to substantially align with an equipotential of the microwave EM energy within the waveguide isolator.

11. A combined isolator-diplexer device according to claim 10, wherein the RF connector comprises a coaxial filter connected to the output section and configured to inhibit microwave EM energy from leaking out of the waveguide isolator through the signal conductor of the RF connector.

12. A combined isolator-diplexer device according to claim 11, wherein the coaxial filter comprises a two section re-entrant coaxial filter.

13. Electrosurgical apparatus for resection of biological tissue, the apparatus comprising:
  a radiofrequency (RF) signal generator for generating RF electromagnetic (EM radiation having a first frequency;
  a microwave signal generator for generating microwave EM radiation having a second frequency that is higher than the first frequency;
  a probe arranged to deliver the RF EM radiation and the microwave EM radiation separately or simultaneously from a distal end thereof; and
  a feed structure for conveying the RF EM radiation and the microwave EM radiation to the probe, the feed structure comprising an RF channel for connecting the probe to the RF signal generator, and a microwave channel for connecting the probe to the microwave signal generator,
wherein the RF channel and microwave channel comprise physically separate signal pathways from the RF signal generator and microwave signal generator respectively,
wherein the feed structure includes an isolator-diplexer device comprising:
  a combining circuit having a first input connected to receive the RF EM radiation from the RF channel, a second input connected to receive the microwave EM radiation from the microwave channel, and an output in communication with the first and second inputs for conveying the RF EM radiation and the microwave EM radiation to the probe along a common signal pathway, and
  a waveguide isolator connected to isolate the microwave channel from the RF EM radiation,
  wherein the waveguide isolator comprises:
    a conductive input section,
    a conductive output section,
    a conductive intermediate section, the intermediate section having a first end which mates with the input section, and a second end which mates with the output section,
    a first DC isolation barrier arranged between the input section and the intermediate section, and
    a second DC isolation barrier arranged between the intermediate section and the output section,
  wherein the input section, intermediate section and output section together enclose a waveguide cavity, wherein the output from the combining circuit includes a signal conductor and a ground conductor, and wherein the first DC isolation barrier and the second DC isolation barrier provide a pair of series-connected capacitive structures between the ground conductor of the output from the combining circuit and the conductive input section of the waveguide isolator, the capacitive structure being arranged to inhibit coupling of the RF EM energy and leakage of the microwave EM energy.

14. Electrosurgical apparatus according to claim 13, wherein the isolator-diplexer device comprises:

the combining circuit having the first input connectable to receive the radiofrequency (RF) electromagnetic (EM) radiation having the first frequency from the RF channel, the second input connectable to receive the microwave EM radiation having the second frequency that is higher than the first frequency from the microwave channel, and the output in communication with the first and second inputs for conveying the RF EM radiation and the microwave EM radiation to the common signal pathway; and wherein the input section, intermediate section and output section are disposed in sequence along a longitudinal direction, wherein the intermediate section overlaps with the input section in the longitudinal direction at the first DC isolation barrier, and wherein the intermediate section overlaps with the output section in the longitudinal direction at the second DC isolation barrier.

* * * * *